United States Patent [19]

Schulze

[11] 3,933,869

[45] Jan. 20, 1976

[54] PREPARATION OF ORGANIC RADIOHALOGEN COMPOUNDS

[75] Inventor: Paul-Eberhard Schulze, Chemiker, Germany

[73] Assignee: Schering Aktiengesellschaft, Berlin, Germany

[22] Filed: Dec. 5, 1973

[21] Appl. No.: 421,818

[30] Foreign Application Priority Data

Dec. 8, 1972 Germany............................ 2260933

[52] U.S. Cl.......................... 260/397.4; 260/397.45
[51] Int. Cl.......................................... C07c 169/20
[58] Field of Search..................... 260/397.4, 397.45

[56] References Cited
UNITED STATES PATENTS 3,644,441  2/1972  Wiechert et al. .............. 260/397.47

OTHER PUBLICATIONS

"Acta Endocrinology," (Copenhagen) 1971, Vol. 68, No. 1, pp. 98–126, as set forth in Chem. Abstracts para. 336h, Vol. 76, 1972, by Gerhards et al.

*Primary Examiner*—Elbert L. Roberts
*Attorney, Agent, or Firm*—Millen, Raptes & White

[57] ABSTRACT

Organic radiohalogen compounds are prepared by heating in a non-aqueous liquid phase a mixture of a radioinactive organic halogen compound and an alkali metal halogenide or alkaline earth halogenide wherein the halogenide is F-18, Cl-38, Br-82 or I-123, -125, -131 or -132.

31 Claims, No Drawings

PREPARATION OF ORGANIC RADIOHALOGEN COMPOUNDS

BACKGROUND OF THE INVENTION

This invention relates to a novel process for the preparation of organic halogen compounds whose halogen atom is radioactive from inactive organic halogen compounds by halogen exchange.

Radioactive-labeled halogen compounds are of great interest, since numerous radioactive diagnostic agents contain a radioactive halogen, especially iodine. Of great significance are thyroxine-$I^{131}$ for thyroid diagnostics, sodium diatrizoate-$I^{131}$ for testing the kidney function, the sodium salt of tetrachlorotetraiodofluorescein-$I^{131}$ for testing the liver function, bromthalein-$I^{131}$ for gall bladder diagnostics, N,N′-hydroxydiacetyl-bis(3-methylamino-2,4,6-triiodobenzoic acid)-$I^{131}$ and N,N′-adipoylbis(3-amino-2,4,6-triiodobenzoic acid)-$I^{131}$ for diagnostic purposes in connection with the liver and gall bladder.

The heretofore known processes for the production of labeled halogen compounds are not universally satisfactory.

In "Nature" 184 (1959), 913, a thermal halogen exchange in an aqueous solution is disclosed. This process is limited to certain specific, water-soluble organic compounds. For example, in this process radioactive iodine can be exchanged in Compound I below, but not in Compounds II and III, although the latter compounds are also water-soluble.

lized and/or additional stages must be incorporated in these methods in order to obtain the labeled compounds. For example, in the production of iodine-tagged tetraiodophthalic acid morpholide, it was necessary to develop a special apparatus (Acta Chem. Scand. 15 (1962), 1139–1142).

In contrast thereto, the novel process of this invention for the preparation of organic radiohalogen compounds is generally applicable to the production of compounds having a wide variety of structures, takes place under gentle conditions, and requires little time.

SUMMARY OF THE INVENTION

According to this invention, a non-radioactive halogen-containing organic compound to be radioactive labeled is heated in the liquid phase in an inert non-aqueous liquid vehicle, e.g., an inert melting solid or a mixture of inert melting compounds or an inert polar organic solvent, with an alkali metal halogenide or an alkaline earth metal halogenide wherein the halogenide is fluorine-18, chlorine-38, bromine-82, or iodine-123,-125,-131, or -132. Both the compounds to be tagged and the metal halogenide are dissolved in the liquid phase.

DETAILED DISCUSSION

The halogenide of the alkali metal halogenides and alkaline earth halogenides employed in the process of this invention are radioactively tagged halogenides.

The term "inert melting solid" means a compound which is inert to the reactants under the reaction condi-

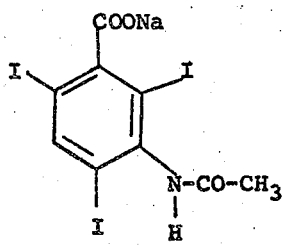

(I)

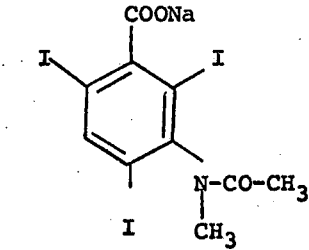

(II)

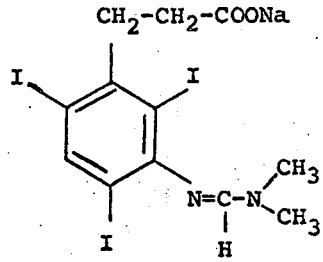

(III)

Moreover, the process described in "Nature" has the disadvantage in practical handling, e.g., in isolation of very small quantities. Moreover difficulties are encountered when producing specifically highly tagged compounds, which are required for scintigraphy.

In several cases, a halogen exchange can also be accomplished on chromatographic columns. However, apart from a limited field of application, these processes are very complicated and time-consuming and disadvantageous with respect to the existing regulations relating to radioprotection.

German Published Application DAS 1,244,185 describes a process for the preparation of carrier-free, iodine-labeled organic compounds in which the halogen compound is exposed, in the presence of carrier-free iodine-131, to the radiation field of a nuclear reactor. However, this method is not feasible in practice, which requires a rapid halogen exchange without simultaneous destruction of the compound to be labeled.

In the synthesis of halogen-tagged organic compounds, conventional methods are generally employed, employing a radio-active precursor compound. Frequently, however, additional techniques must be utitions. In every instance, the reaction is conducted at a temperature at or above its melting point. Suitable melting substances are those having a maximally broad melting range, e.g., from 30° to 300° C., preferably 60° to 200° C. The melting substances must be stable at the reaction temperature and must not enter into any chemical reactions with the substrate. Examples of suitable melting compounds are N,N-dimethyl-p-toluenesulfonamide, N,N′-bis(dimethylamino) sulfone, dimethylsulfone, and mixtures thereof.

The term "inert polar solvent" means a compound which is inert to the reactants and in which the starting organic halogen compound and the metal halogenide are soluble under the reaction conditions, which is a liquid at ambient temperature.

The term "liquid phase" means the starting organic halogen compound is either a liquid, or is dissolved in the liquid vehicle under the reaction conditions. The term "non-aqueous" means the reaction is conducted in the substantial absence of water, i.e., under substantially anhydrous conditions.

Depending on whether one or more melting compounds or a polar solvent is employed, the liquid phase is either in the form of a melt or the starting organic solution. A melt is preferred. Although organic halogen compounds, especially iodine compounds usually melt with decomposition, they can be heated as a melt in the melting compound to above their melting point without decomposing.

The reaction is effected at a temperature of from 30° to 300° C., preferably 60° to 200° C. The halogen exchange is terminated after a few minutes to several hours. The rate of exchange of radiohalogenide can be up to 100%, the exact amount being dependent on the selected starting organic halogenide, the reaction temperature and the reaction period.

In carrying out the process of this invention employing a melting compound or compounds, it is melted either alone or in the presence of either the starting radiohalogenide or the starting organic halide to be tagged. Then the remaining reactant is added thereto. The radiohalogenide must be dissolved in the melt in order to ensure a satisfactory reaction rate. Because these salts can be dissolved only with difficulty in melts of most melting compounds, a convenient method of achieving this is to add the radiohalogenide as an aqueous solution in a minimum amount of water, and the water is thereafter removed before reaction of the radiohalogenide with the organic halogen compound.

Examples of preferred polar organic solvents which can be employed in the process of this invention are dimethylacetamide and N-benzyl-N-methylaniline.

Because the reaction is conducted under anhydrous conditions, the water must then be removed, e.g., by evaporation, before initiating the radiohalogenide exchange reaction. The aqueous radioactive halogenide solution in the reaction vessel can also be brought to dryness prior to the melting step.

The reaction is preferably conducted in a protective inert gas atmosphere, e.g., dry nitrogen or argon.

When employing a polar organic solvent, a similar procedure can be employed if the starting radiohalogenide is difficultly soluble therein, i.e., distilling or evaporating the water employed in rendering the radiohalogenide soluble in the polar solvent. However, with the preferred polar solvents, aqueous solutions of the starting radiohalogenide are not required.

The starting alkali metal and alkaline earth halogenides include the Na, K, Li, Ca and Ba salts of each of the radioactive halogen isotopes listed herein. The radiohalogenides are employed substantially carrier-free, i.e., the pure isotope, substantially free from the non-radioactive isotope, is employed.

The molar proportion of metal halogenide to organic halogen compound employed in the process of this invention depends on the degree of radioactive tagging desired.

By the process of this invention, it is possible not only to tag halogen-containing organic compounds with the customary halogen isotopes within 2-3 hours, but also renders iodine isotope 123, which has a half-life period of 13 hours, generally applicable for radioactive diagnostic purposes by enabling it to be incorporated into a wide variety of organic halogen compounds. The iodine isotopes 123 and 132 heretofore could be exchanged against natural non-radioactive iodine, in accordance with the conventional methods, only if the exchange periods were brief and were generally unusable for the synthesis of iodine-tagged compounds to be synthesized. Iodine-123, due to lack of a β-radioation and the favorable energy of the γ-radiation, and its identity with the body iodine, is of great significance particularly with respect to heretofore employed auxiliary isotopes, such as technetium-99m, which is an artificial element for the human body and does not have any bond to organic carbon compounds.

In all cases where the starting radioinactive substrate contains a halogen different from the radiohalogen of the metal halogenide isotope utilized for the exchange, it is possible to obtain carrier-free tagged substances with a radioisotope, in accordance with this invention. Thus, it is possible, for example, to exchange a natural (fluorine-19) fluorine atom in the starting organic compound not only against fluorine-18, but also against a radioactive chlorine, bromine, or iodine isotope.

Halogen-containing steroids can be radiohalogen-labeled according to the process of this invention. Tagged corticolds, such as 6α-fluoro- and 6β-iodo-21-acetoxy-11β-hydroxy-16α-methyl-1,4-pregnadiene-3,20-dione are, for example, agents for the detection and location of specific foci of inflammation. Halogen-labeled progestational agents, such as 6-chloro- and 6-iodo-17α-acetoxy-1α,2α-methylene-4,6-pregnadiene-3,20-dione, are suitable as agents for diagnosis by scintigraphy.

This invention also relates to the following such novel radiohalogen-labeled steroid hormones: 6α-halo-21-acetoxy-11β-hydroxy-16α-methyl-1,4-pregnadiene-3,20-dione, wherein the halogen atom is iodine-123, -125, -131 or -132, or fluorine at least a portion of which is fluorine-18, and 6-halo-17α-acetoxy-1α,2α-methylene-4,6-pregnadiene-3,20-dione, wherein the halogen atom is iodine-123, -125, -131, or -132 or chlorine at least a portion of which is chlorine-38.

Without further elaboration, it is believed that one skilled in the art can, using the preceding description, utilize the present invention to its fullest extent. The following preferred specific embodiments are, therefore, to be construed as merely illustrative, and not limitative of the remainder of the specification and claims in any way whatsoever.

EXAMPLE 1

At 80° C., 100 mg. of N,N-dimethyl-p-toluenesulfonamide (m.p. 79°–80°C.) is melted and combined with the desired amount of activity, for example 5 m Ci of sodium iodide, maximally carrier-free (wherein the iodide is present as I-123, I-125, I-131, I-132), in an aqueous solution. The water is driven off under a slight nitrogen stream. 100 mg. of β-[3-(N,N-dimethylformamidino)-2,4,6-triiodophenyl]-propionic acid is placed on top of the clear melt, and the temperature is increased to 120° C. while providing a nitrogen atmosphere. A clear melt having a small sediment is thus produced. After 2 hours, the reaction mixture is allowed to cool, the solidified mass is dissolved in acetone, and the solution is poured into 5 ml. of 2N ammonia solution. After the mixture has been filtered off from the insoluble N,N-dimethyltoluenesulfonamide, it is acidified, and the precipitated β-[3-(N,N-dimethylformamidino)-2,4,6-triiodophenyl]-propionic acid is filtered and dried. The substance corresponds in its degree of purity chemically to the starting material and, as confirmed by dilution analysis, is radiochemically purer than 99%. The activity exchange is > 90%, the recovery of the substance is 100%.

EXAMPLE 2

100 mg. of hexaiodobenzene is melted in 300 mg. of N,N-dimethyltoluenesulfonamide; a sediment remains during this step. After adding 5 m Ci of carrier-free sodium iodide-131 or another iodine isotope and removing the water by vaporization, the reaction mixture is heated under nitrogen for 3 hours to 150° C. The solidified melt is taken up in methanol, and the insoluble matter is filtered after extraction. The recovery of hexaiodobenzene is 100%, the activity exchange is 66%.

EXAMPLE 3

Analogously to Example 1, β-[3-(N,N-dimethylformamidino)-2,4,6-triiodophenyl]-propionic acid is treated in dimethylsulfone at 140° C. for 3 hours with carrier-free sodium iodide-131 or another iodine isotope. The β-[3-(N,N-dimethylformamidino)-2,4,6-triiodophenyl]-propionic acid is recovered to an extent of 100%. The exchange rate is 70%.

EXAMPLE 4

Analogously to Example 1, 500 mg. of N,N'-hydroxydiacetyl-bis(3-methylamino-2,4,6-triiodobenzoic acid) is treated at 100° C. The reaction takes 3 hours, providing 100% recovery of the acid employed; the exchange rate is 70%.

EXAMPLE 5

As described in Example 1, 10 mg. of tetrachlorotetraiodofluorescein is dissolved in 100 mg. of N,N-dimethyltoluenesulfonamide and treated at 90° C. for 10 minutes with potassium iodide-125 or another iodine isotope. Recovery of the tetrachlorotetraiodofluorescein is 100%, the rate of exchange is more than 80%.

EXAMPLE 6

100 mg. of 6-chloro-17α-acetoxy-1α,2α-methylene-4,6-pregnadiene-3,20-dione in 200 mg. of N,N-dimethyltoluenesulfonamide is treated, as set forth in Example 1, for 3 hours at 120° C. with sodium iodide-131 or another iodine isotope. In the thin-layer system of cyclohexane/ethyl acetate 60 : 90, the thus-obtained 6-iodine compound is separated. This compound is labeled with the iodine isotope employed in position 6, carrier-free; the rate of exchange is about 50%.

EXAMPLE 7

Analogously to Example 1, 500 mg. of iodomethanesulfonic acid is treated for 3 hours at 120° C. with sodium iodide-125 and worked up by way of the sodium salt. The recovery of iodomethanesulfonic acid is 100%, the activity exchange is more than 90%.

EXAMPLE 8

500 mg. of β-[3-(N,N-dimethylformamidino)-2,4,6-triiodophenyl]-propionic acid is treated in 1 ml. of dimethylacetamide for 3 hours at 120° C. with sodium iodide-131. After the dimethylacetamide has been removed under vacuum, the mixture is worked up as usual. Recovery of the β-[3-(N,N-dimethyl-formamidino)-2,4,6-triiodophenyl]-propionic acid is 100%, the exchange rate is 30%.

EXAMPLE 9

50 mg. of 6 α-fluoro-21-acetoxy-11β-hydroxy-16α-methyl-1,4-pregnadiene-3,20-dione (fluocortolone acetate) is dissolved in 100 mg. of N,N-dimethyltoluenesulfonamide and treated, as set forth in Example 1, for 3 hours at 180° C. with sodium iodide-131 or another iodine isotope. After separation by preparative thin-layer analysis, the product is 6 α-iodo-21-acetoxy-11β-hydroxy-16α-methyl-1,4-pregnadiene-3,20-dione which is tagged, carrier-free, in the 6 position with iodine-131 isotope. The rate of exchange is about 20%.

EXAMPLE 10

50 mg. of 6 α-fluoro-21-acetoxy-11β-hydroxy-16α-methyl-1,4-pregnadiene-3,20-dione (fluocortolone acetate) is dissolved in 100 mg. of N,N-dimethyltoluenesulfonamide and treated as described in Example 1 for 3 hours at 180° C. with sodium fluoride-18. The product is fluocortolone acetate tagged with fluorine-18 in the 6 position. The rate of exchange is about 5%.

EXAMPLE 11

100 mg. of 2,4,6-trichloro-3-acetylaminobenzoic acid is treated analogously to Example 1 with sodium bromide-82 at 150°C. The reaction takes 6 hours; the acid utilized is recovered with 100%; the rate of exchange is 30%.

EXAMPLE 12

Analogously to Example 1, β-[3-(N,N-dimethylformamidino)-2,4,6-triiodophenyl]-propionic acid in dimethylsulfone and N,N'-bis(dimethylamino)sulfone —respectively 300 mg. at 50° C. — are treated for 3 hours with carrier-free sodium iodide-131 or another iodine isotope. The β-[3-(N,N-dimethylformamidino)-2,4,6-triiodophenyl]-propionic acid is recovered to an extent of 100%. The rate of exchange is 70%.

EXAMPLE 13

Analogously to Example 1, 100 mg. of L-thyroxine is treated for 30 minutes at 100° C. The L-thyroxine is recovered with 80%; the rate of exchange is 80%.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of organic radiohalogen compounds from radioinactive the corresponding organic halogen compounds by halogen exchange, which comprises heating in the liquid phase a radioinactive organic halogen compound under non-aqueous conditions with an alkali metal halogenide or alkaline earth halogenide wherein the halogenide is fluorine-18, chlorine-38, bromine-82 or iodine-123, -125, -131 or -132.

2. A process according to claim 1 wherein the radioinactive organic halogen compound to be tagged is heated in a melt of one or more inert compounds having a melting point of 60°–200° C. and the radioactive halogenide is substantially carrier-free.

3. A process according to claim 2 wherein the halogenide is added as an aqueous solution to the inert compound or mixture of compounds which is formed into a melt and the water is thereafter removed before formation of the melt and reaction of the alkaline earth halogenide with the organic halogen compound.

4. A process according to claim 2 wherein the inert compound or mixture of compounds which is formed into a melt is N,N-dimethyl-p-toluenesulfonamide, N,N'-bis(dimethylamino)sulfone, dimethylsulfone, or a mixture thereof.

5. A process according to claim 1 wherein the reaction is conducted in a polar organic solvent.

6. A process according to claim 5 wherein the organic polar solvent is dimethylacetamide or N-methyl-N-benzyl-aniline.

7. A process according to claim 1 wherein organic radioactive halogen compounds are produced by the exchange of halogen in the organic halogen compound against a different halogen present in radioactive form in the alkaline earth halogenide.

8. A process according to claim 7 wherein the alkaline earth halogenide is iodine-123.

9. 6α-Halo-21-acetoxy-11β-hydroxy-16α-methyl-1,4-pregnadiene-3,20-dione wherein the halogen atom is iodine-123, -125, -131 or -132 or fluorine at least a portion of the 6α-fluorine is fluorine-18.

10. A compound of claim 9, 6α-(iodine-131)-21-acetoxy-11β-hydroxy-16α-methyl-1,4-pregnadiene-3,20-dione.

11. A compound of claim 9, 6α-(iodine-123)-21-acetoxy-11β-hydroxy-16α-methyl-1,4-pregnadiene-3,20-dione.

12. A compound of claim 9, 6α-(iodine-125)-21-acetoxy-11β-hydroxy-16α-methyl-1,4-pregnadiene-3,20-dione.

13. A compound of claim 9, 6α-(iodine-132)-21-acetoxy-11β-hydroxy-16α-methyl-1,4-pregnadiene-3,20-dione.

14. A compound of claim 9, 6α-fluoro-21-acetoxy-11β-hydroxy-16α-methyl-1,4-pregnadiene-3,20-dione wherein at least a portion of the 6α-fluorine is fluorine-18.

15. 6-Halo-17α-acetoxy-1α,2α-methylene-4,6-pregnadiene-3,20-dione wherein the halo atom is iodine-123, -125, -131 or -132 or chlorine at least a portion of the 6-chlorine is chlorine-38.

16. A compound of claim 15, 6-(iodine-131)-17α-acetoxy-1α, 2α-methylene-4,6-pregnadiene-3,20-dione.

17. A compound of claim 15, 6-(iodine-123)-17α-acetoxy-1α, 2α-methylene-4,6-pregnadiene-3,20-dione.

18. A compound of claim 15, 6-(iodine-125)-17α-acetoxy-1α, 2α-methylene-4,6-pregnadiene-3,20-dione.

19. A compound of claim 15, 6-(iodine-132)-17α-acetoxy-1α, 2α-methylene-4,6-pregnadiene-3,20-dione.

20. A compound of claim 15, 6-chloro-17α-acetoxy-1α,2α-methylene-4,6-pregnadiene-3,20-dione wherein at least a portion of the 6-chlorine is chlorine-38.

21. A process according to claim 1 wherein the organic halogen compound is a steroid.

22. A process according to claim 21 wherein the steroid is of the pregnane series.

23. A process according to claim 22 wherein the steroid is a 6-halo steroid.

24. A process according to claim 1 wherein the halogen compound is β-[3-(N,N-dimethylformamidino)-2,4,6-triiodophenyl)-propionic acid.

25. A process according to claim 1 wherein the halogen compound is hexaiodobenzene.

26. A process according to claim 1 wherein the halogen compound is β-[3-(N,N-dimethylformamidino)-2,4,6-triiodophenyl]-propionic acid.

27. A process according to claim 1 wherein the halogen compound is N,N'-hydroxydiacetyl-bis(3-methylamino-2,4,6-triiodobenzoic acid).

28. A process according to claim 1 wherein the halogen compound is tetrachlorotetraiodofluorescein.

29. A process according to claim 1 wherein the halogen compound is iodomethanesulfonic acid.

30. A process according to claim 1 wherein the halogen compound is 2,4,6-trichloro-3-acetylaminobenzoic acid.

31. A process according to claim 1 wherein the halogen compound is L-thyroxine.

* * * * *